United States Patent
Porter et al.

(10) Patent No.: US 11,413,407 B2
(45) Date of Patent: Aug. 16, 2022

(54) AEROSOL DELIVERY DEVICE

(71) Applicant: Stamford Devices Ltd., Dangan (IE)

(72) Inventors: Shaun Porter, Dangan (IE); Louise Sweeney, Dangan (IE); Ronan MacLoughlin, Dangan (IE); Jim Fink, San Mateo, CA (US); Aidan Duffy, Dangan (IE); Claire Lillis, Dangan (IE); Conor Duffy, Dangan (IE); Fran Keating, Dangan (IE)

(73) Assignee: STAMFORD DEVICES LTD., Dangan (IE)

(*) Notice: Subject to any disclaimer, the term of this patent is extended or adjusted under 35 U.S.C. 154(b) by 321 days.

(21) Appl. No.: 15/933,205

(22) Filed: Mar. 22, 2018

(65) Prior Publication Data

US 2018/0272079 A1    Sep. 27, 2018

Related U.S. Application Data (60) Provisional application No. 62/475,635, filed on Mar. 23, 2017, provisional application No. 62/475,603, (Continued)

(51) Int. Cl.
*A61M 11/00* (2006.01)
*A61M 16/00* (2006.01)
(Continued)

(52) U.S. Cl.
CPC ......... *A61M 11/005* (2013.01); *A61M 11/001* (2014.02); *A61M 15/0085* (2013.01);
(Continued)

(58) Field of Classification Search
CPC ...... A61M 11/00–044; A61M 16/0003; A61M 16/021–026; A61M 15/0085;
(Continued)

(56) References Cited

U.S. PATENT DOCUMENTS 2,855,244 A * 10/1958 Camp ................. B05B 17/063
239/102.2
6,769,626 B1 * 8/2004 Haveri ................ A61M 11/005
239/102.2
(Continued)

FOREIGN PATENT DOCUMENTS

EP    0516565 A1    2/1992
EP    2149359 A1    2/2010
(Continued)

OTHER PUBLICATIONS

Takahashi, JP0725617A-English Machine Translation, Accessed Mar. 2, 2020 (Year: 2020).*

(Continued)

*Primary Examiner* — Elliot S Ruddie
(74) *Attorney, Agent, or Firm* — Kilpatrick Townsend & Stockton LLP (57) ABSTRACT

An aerosol delivery system that includes an aerosol generator that aerosolizes a fluid for delivery to a patient. The aerosol generator includes a housing with a fluid chamber that fluidly communicates with a housing inlet and a housing outlet. Within the housing, the aerosol generator includes a support plate with an aperture that fluidly communicates with the housing outlet. A vibratable member couples to the support plate across the aperture. A piezoelectric actuator also couples to the support plate, and in operation expands and contracts to vibrate the vibratable member, which aerosolizes a fluid. The aerosol generator receives fluid through a fluid conduit that couples to the housing.

15 Claims, 9 Drawing Sheets

Related U.S. Application Data filed on Mar. 23, 2017, provisional application No. 62/475,618, filed on Mar. 23, 2017.

(51) Int. Cl.

| | |
|---|---|
| *A61M 16/06* | (2006.01) |
| *A61M 16/04* | (2006.01) |
| *A61M 16/14* | (2006.01) |
| *A61M 16/08* | (2006.01) |
| *B05B 17/00* | (2006.01) |
| *A61M 15/00* | (2006.01) |
| *A61M 15/08* | (2006.01) |
| *A61M 16/16* | (2006.01) |
| *B05B 12/08* | (2006.01) |

(52) U.S. Cl.
CPC ........ *A61M 15/08* (2013.01); *A61M 16/0003* (2014.02); *A61M 16/022* (2017.08); *A61M 16/026* (2017.08); *A61M 16/0465* (2013.01); *A61M 16/0488* (2013.01); *A61M 16/0666* (2013.01); *A61M 16/0672* (2014.02); *A61M 16/0816* (2013.01); *A61M 16/14* (2013.01); *B05B 17/0646* (2013.01); *A61M 16/04* (2013.01); *A61M 16/16* (2013.01); *A61M 2016/0018* (2013.01); *A61M 2016/0021* (2013.01); *A61M 2016/0027* (2013.01); *A61M 2016/0033* (2013.01); *A61M 2016/0039* (2013.01); *A61M 2016/0042* (2013.01); *A61M 2202/0488* (2013.01); *A61M 2205/17* (2013.01); *A61M 2205/332* (2013.01); *A61M 2205/3303* (2013.01); *A61M 2205/3327* (2013.01); *A61M 2205/3334* (2013.01); *A61M 2205/3368* (2013.01); *A61M 2205/3375* (2013.01); *A61M 2205/3569* (2013.01); *A61M 2205/3592* (2013.01); *A61M 2205/505* (2013.01); *A61M 2209/045* (2013.01); *A61M 2209/084* (2013.01); *A61M 2230/40* (2013.01); *A61M 2230/432* (2013.01); *A61M 2230/50* (2013.01); *A61M 2230/63* (2013.01); *A61M 2240/00* (2013.01); *B05B 12/08* (2013.01)

(58) Field of Classification Search
CPC .............. A61M 15/08; A61M 16/0465; A61M 16/0666–0672; A61M 16/0816; A61M 16/14; A61M 16/04; A61M 16/16; A61M 2016/0015–0021; A61M 2016/0027; A61M 2016/003–0042; A61M 2202/0488; A61M 2205/17; A61M 2205/32–3303; A61M 2205/3327–3334; A61M 2205/3368; A61M 2205/3375; A61M 2205/3569; A61M 2205/3592; A61M 2205/505; A61M 2209/045; A61M 2209/084; A61M 2230/40–432; A61M 2230/50; A61M 2230/63; A61M 2240/00; B05B 17/0638–0646; B05B 12/00; B05B 17/06–0684

USPC ....................... 128/200.16; 239/102.1, 102.2
See application file for complete search history.

(56) References Cited

U.S. PATENT DOCUMENTS

| | | | |
|---|---|---|---|
| 2010/0206306 A1* | 8/2010 | Feriani | A61M 15/0085 128/203.12 |
| 2011/0315786 A1 | 12/2011 | Kambayashi | |
| 2012/0125334 A1 | 5/2012 | Korneff et al. | |
| 2013/0079732 A1* | 3/2013 | Burt | B05B 7/0012 604/290 |
| 2014/0116427 A1* | 5/2014 | Pevler | A61M 11/02 128/200.18 |
| 2015/0165146 A1 | 6/2015 | Bowman et al. | |
| 2016/0228656 A1 | 8/2016 | Vasandani et al. | |

FOREIGN PATENT DOCUMENTS

| | | | | |
|---|---|---|---|---|
| FR | 2929861 A1 | 10/2009 | | |
| JP | 07256170 A | * 10/1995 | ........... | B05B 17/063 |
| JP | 2003520079 A | 7/2003 | | |
| JP | 2013-511382 A | 4/2013 | | |
| JP | 5-329411 B2 | 10/2013 | | |
| RU | 2519959 C2 | 6/2014 | | |
| WO | 2012046220 A1 | 4/2012 | | |
| WO | 2012-063951 A1 | 5/2012 | | |
| WO | 2013-158967 A2 | 10/2013 | | |
| WO | 2017021536 A2 | 2/2017 | | |

OTHER PUBLICATIONS

Merriam-Webster, "Defines", accessed Oct. 8, 2020 (Year: 2020).*
Response to Invitation to Pay Additional Fees dated Jun. 14, 2018 in PCT/EP2018/057559, all pages.
International Search Report and Written Opinion dated Aug. 13, 2018 in PCT/EP2018/057559, all pages.
Examination Report for EP 18 714 745.9 dated May 21, 2021, all pages.
Office Action for Russian Patent Appln. No. 2019133441, dated Apr. 13, 2021, all pages.
Notice of Publication No. for Russian Patent Appln. No. 2019133441 dated Apr. 23, 2021 in the Official Bulletin of the Russian Patent Office No. 12. The Applicant is not in possession of a translation of the publication.
Office Action for RU 2019133441 issued by the Patent Office of the Russian Federation dated Jul. 26, 2021, all pages.
Second Office Action issued for Chinese application No. 201880034200.5 dated Nov. 3, 2021, all pages.
Office Action issued for Russian application No. 2019133441 received Nov. 11, 2021, all pages.
Office Action issued for Japanese application No. 2019-552612 dated Dec. 1, 2021, all pages.
First Examination Report for Indian Patent Appln. No. 201917042603 dated Jan. 7, 2022, 7 pages.
Final Office Action dated May 10, 2022 received for Japanese Patent Appln. No. 2019-552612, all pages.

* cited by examiner

AEROSOL DELIVERY DEVICE

CROSS REFERENCE TO RELATED APPLICATIONS

This application claims priority to U.S. Application No. 62/475,618, filed Mar. 23, 2017, entitled Retrofit Aerosol Delivery System and Method, U.S. Application No. 62/475,635, filed Mar. 23, 2017, entitled Aerosol Delivery Device, and U.S. Application No. 62/475,603, filed Mar. 23, 2017, entitled Aerosol Delivery System and Method, the entire contents of which are incorporated by reference herein.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

There are many types of respiratory diseases that can affect the ability of patients to breathe normally. These diseases may range from a common cold to cystic fibrosis. Modern medicine treats these diseases in a variety of ways including oral medication, inhalers, nebulizers, etc. A nebulizer is a device that changes fluid (i.e., medicament) into an aerosol for delivery to a patient through breathing. The patient may receive the aerosol through the mouth, nose, and/or a tracheotomy (i.e., a surgically made cut in the throat). However, a nebulizer may not effectively treat a respiratory disease if the aerosol droplets are large and/or the aerosol formation is not properly timed with a patient's breathing cycle.

SUMMARY OF THE INVENTION

In some embodiments, an aerosol delivery system includes an aerosol generator that aerosolizes a fluid for delivery to a patient. The aerosol generator includes a housing with a fluid chamber that fluidly communicates with a housing inlet and a housing outlet. The aerosol generator includes a support plate with an aperture. A vibratable member couples to the support plate so as to be positioned across the aperture. A piezoelectric actuator also couples to the support plate, and in operation expands and contracts to vibrate the vibratable member, which aerosolizes a fluid. In this way, when a fluid is supplied to a surface of the vibratable member, the fluid is turned into an aerosol and that is then available for delivery through the housing outlet. The aerosol generator receives the fluid through a fluid conduit that couples to the housing.

The fluid conduit is spaced away from the vibratable member at a distance that attracts the fluid to the vibratable member as it exits the fluid delivery conduit (e.g., through surface tension). The fluid delivery conduit is therefore able to transfer fluid to the vibratable member in any orientation or substantially all orientations of the aerosol generator. The distance may also be tuned to block or reduce the ability of the vibratable member to draw/remove undispensed fluid from the fluid delivery conduit (e.g., as the vibratable member vibrates changing the distance between the end of the fluid delivery conduit and the vibratable member). The distance may also be tuned to control the spreading of fluid over the vibratable member. For example, the closer the fluid delivery conduit is to the vibratable member the interaction between the vibratable member, the fluid, and the fluid delivery conduit may reduce the ability of the fluid to spread. As will be explained in additional detail below, when the fluid spreads over a greater surface area more apertures in the vibratable member are exposed to fluid, which may change the characteristics of the aerosol.

In another embodiment, an aerosol delivery system includes an aerosol generator that aerosolizes a fluid for delivery to a patient. The aerosol generator includes a housing with a fluid chamber that fluidly communicates with a housing inlet and a housing outlet. The aerosol generator includes a support plate with an aperture. A vibratable member couples to the support plate so as to be positioned across the aperture. A piezoelectric actuator also couples to the support plate, and in operation expands and contracts to vibrate the vibratable member, which aerosolizes a fluid. In this way, when a fluid is supplied to a surface of the vibratable member, the fluid is turned into an aerosol that is then available for delivery through the housing outlet. The aerosol generator receives fluid through a plurality of conduits that deliver the fluid to the vibratable member.

The plurality of conduits may facilitate rapid distribution of fluid over a surface of the vibratable member as well as controlled distribution of liquid across the surface of the vibratable member (e.g., some portions of the vibratable member may receive more fluid than others). The plurality of conduits extend into the housing and are a distance from the vibratable member that ensures that the vibratable member attracts the fluid exiting the plurality of conduits (e.g., through surface tension). In this way, the fluid can be transferred to the vibratable member in any orientation or substantially all orientations. The distance may also be tuned to block or reduce the ability of the vibratable member to draw/remove undispensed fluid from the plurality of conduits (e.g., as the vibratable member vibrates changing the distance between the ends/outlets of the plurality of conduits and the vibratable member). In other words, the distance may facilitate accurate fluid release for aerosolization. The distance may also be tuned to control the spread of fluid over the vibratable member. For example, the closer the plurality of conduits are to the vibratable member the friction between the vibratable member, the fluid, and the plurality of conduits may reduce the ability of the fluid to spread. In some embodiments, one or more of the plurality of conduits may be placed at different distances from the vibratable member and/or have different sizes. Accordingly, some of the plurality of conduits may enable more rapid spreading of fluid over portions of the vibratable member while others may reduce the spread of fluid over other portions of the vibratable member.

An aspect of the disclosure includes a method for aerosolizing a fluid. The method includes supplying a volume of fluid to a surface of a vibratable member in an aerosol generator such that the fluid adheres to the surface by surface tension forces. The method converts the fluid into an aerosol by vibrating the vibratable member with a piezoelectric actuator. By supplying a volume of liquid that adheres to the surface of the vibratable member, no reservoir of liquid is required to be stored at the surface. In this way, the aerosol generator can be moved to any position and still be able to aerosolize the liquid. Further, loss of expensive medications may be minimized since the liquid is supplied and aerosolized on an on-demand basis.

BRIEF DESCRIPTION OF THE DRAWINGS

Various features, aspects, and advantages of the present invention will be better understood when the following detailed description is read with reference to the accompanying figures in which like characters represent like parts throughout the figures, wherein.

DETAILED DESCRIPTION

One or more specific embodiments of the present invention will be described below. These embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The embodiments discussed below include an aerosol delivery system capable of predicting inhalation by a patient in order to time production and delivery of an inhalable medicament. For example, the aerosol delivery system may predict inhalation so that the medicament can be aerosolized before inhalation. By aerosolizing the medicament before inhalation the aerosol delivery system may increase the amount of medication delivered to the patient per breath, enhances the effectiveness of the medication, and/or delivers the medication to a greater area within a patient's lungs (e.g., deeper into the lungs). The aerosol delivery system uses one or more breath sensors to detect inhalation by a patient. These breath sensors may detect inhalation across all ventilation modes including mandatory, assisted, and spontaneous. For example, the aerosol delivery system may use a flow sensor as the breath sensor to detect inhalation by a patient. As will be explained below, flow sensors are more effective than pressure sensors at detecting the start and stop of inhalation.

The aerosol delivery system may also increase delivery effectiveness with an aerosol generator capable of producing fine particle fractions (FPF) greater than 80% with droplets/particles having a volume median diameter (VMD) of 1 micron or less. In other words, the aerosol generator is capable of producing very fine aerosols that are easily suspended in and carried by a carrier fluid (e.g., air, O2, O2/air mixture, etc.). Finally, the aerosol delivery systems discussed below may couple to existing respiratory systems without redesigning or reengineering those systems. This enables the aerosol delivery system to be used with existing ventilators, humidifiers, continuous positive airway pressure (CPAP) machines, etc.

As will be discussed in detail below, the aerosol delivery system includes an aerosol generator that receives a supply of fluid that adheres to a rear surface of a vibratable member, so that no reservoir of liquid is required to be stored at the rear surface. In this way, the aerosol generator can be moved to any position and still be able to aerosolize the fluid. Further, loss of expensive medications may be minimized since the fluid is supplied and aerosolized on an on-demand basis.

The fluid is supplied through one or more fluid conduits. The conduit or conduits extend into a housing of an aerosol generator and are spaced a distance from a vibratable member that ensures that the vibratable member attracts the fluid exiting the plurality of conduits (e.g., through surface tension). In this way, the fluid can be transferred to the vibratable member in any orientation or substantially all orientations. The distance may also be tuned to block or reduce the ability of the vibratable member to draw/remove undispensed fluid from the conduit(s). The distance may also be tuned to control the spread of fluid over the vibratable member. For example, the closer the conduit(s) are to the vibratable member the friction between the vibratable member, the fluid, and the conduit(s) may reduce the ability of the fluid to spread.

The vibratable member may also be customized to produce aerosols with different characteristics (e.g., VMD, plume velocity, plume density, average flowrate, direction, etc.). For example, different vibratable members may differ in the size, number, location, etc. of apertures. In some embodiments, customization may enable generation of different aerosols at different locations on the vibratable member. That is portions of the same vibratable member may differ in the number and size of apertures so that different portions of the vibratable member may produce aerosols with different sizes, densities, etc. The ability to customize the vibratable member facilitates aerosol generation for different fluids, different treatments, different applications, etc.

Figure 1:
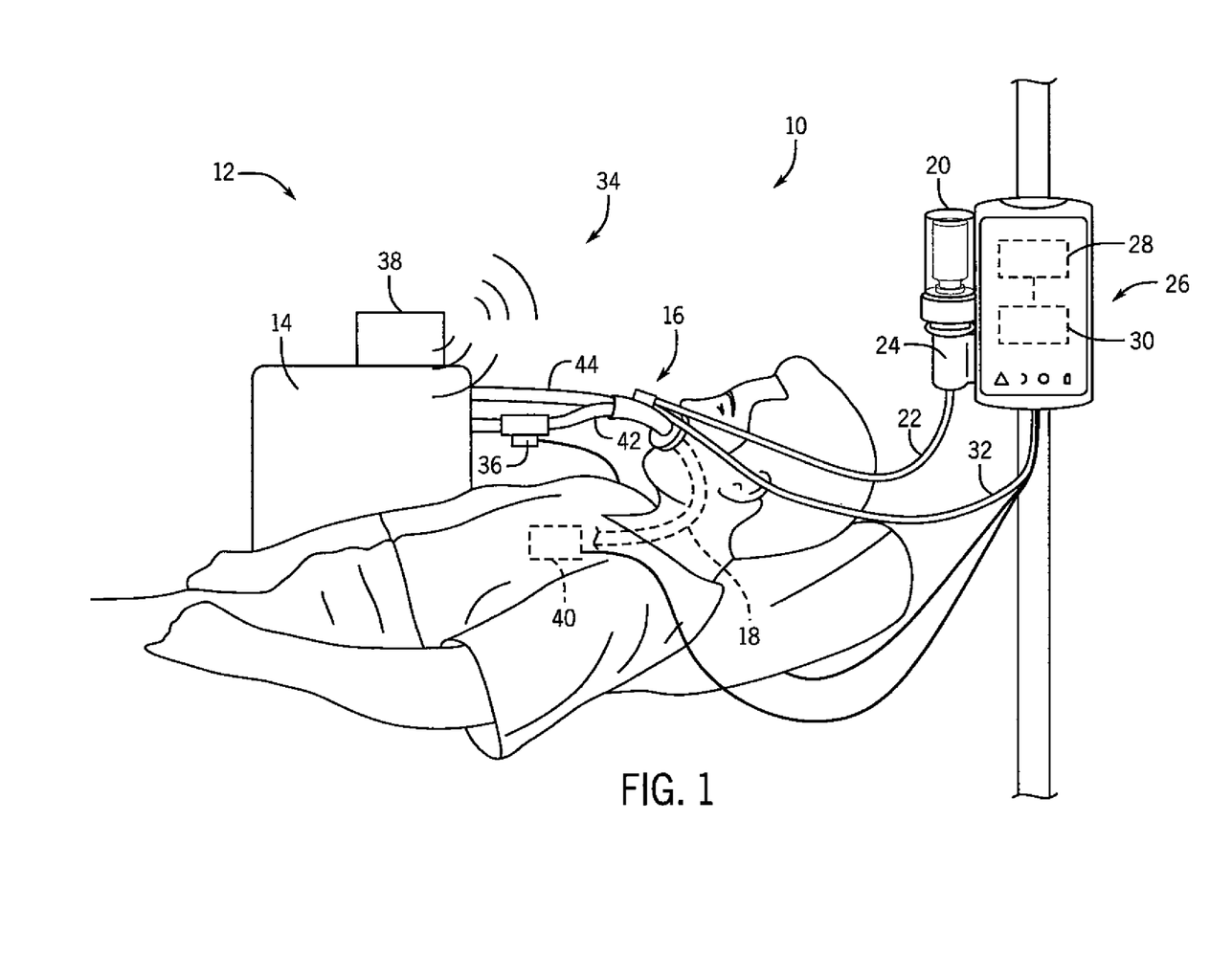
FIG. 1 is a schematic view of an embodiment of an aerosol delivery system connected to a respiratory system.

FIG. 1 is a schematic view of an embodiment of an aerosol delivery system 10 connected to a respiratory system 12. In FIG. 1, the respiratory system 12 includes a ventilator 14 capable of forcing air (e.g., air, O2, air/O2 mixture, etc.) into and withdrawing air from a patient. As will explained in detail below, the aerosol delivery system 10 is capable of connecting to a variety of existing respiratory systems 12 to provide aerosolized fluid (e.g., medicament) for patient treatments. That is the aerosol delivery system 10 may be retrofitted to existing respiratory systems 12 (e.g., ventilators, humidifiers, continuous positive airway pressure (CPAP) machines, or combinations thereof) without redesigning or reengineering the respiratory system 12 to work with the aerosol delivery system 10.

The aerosol delivery system 10 includes an aerosol generator 16 capable of coupling to a variety of airflow devices such as endotracheal tubes 18, nasal cannula/masks, tracheostomy tubes, etc. The aerosol generator 16 receives fluid from a fluid source 20 through a fluid delivery conduit 22. The fluid source 20 (e.g., container, vial) may contain a variety of substances including medicament, surfactant, a combination thereof, etc. In operation, fluid from the fluid source 20 is pumped with a pump 24 through the fluid delivery conduit 22 to the aerosol generator 16 where the fluid is aerosolized before and/or while the patient inhales. In some embodiments, the fluid delivery conduit 22 may be primed with fluid before treatment to ensure rapid delivery (e.g., preloading fluid in aerosol generator 16). The pump 24 is controlled with a controller 26 which times delivery and dosage of the fluid.

The controller 26 includes one or more processors 28 that execute instructions stored on one or more memories 30 to drive operation of the pump 24 and the aerosol generator 16. For example, the memory 30 may include instructions that indicate the amount of fluid to be pumped to the aerosol generator 16 in each dose for each actuation of the aerosol generator, how much fluid is to be pumped over a specific period of time or times, etc. The stored instructions may be based on a size of the patient, age of the patient, sex of the patient, type of medicament, fluid additives, desired amount of aerosol, etc. The memory 30 also includes instructions for activating the aerosol generator 16. As illustrated, the controller 26 connects to the aerosol generator 16 with a cable 32 (i.e., electric cable) and/or using wireless connections. The cable 32 carries a signal that activates a piezoelectric (or other) actuator inside the aerosol generator 16. As the piezoelectric actuator operates, it vibrates a vibratable member that then aerosolizes the fluid for delivery to the patient (i.e., through inhalation). The memory may therefore include instructions for controlling when the piezoelectric actuator starts, stops, vibration frequency or frequencies, etc.

The aerosol delivery system 10 increases treatment effectiveness by timing the creation of the aerosol. For example, the aerosol delivery system 10 may begin aerosolizing the medicament before the patient inhales. In this way, the aerosol delivery system 10 takes advantage of the increased airflow at the start of inhalation. This increases the medicament delivery to the patient as the inhaled air carries the medicament farther into the patient's lungs. The aerosol delivery system 10 may also aerosolize medicament as soon as inhalation is detected (e.g., for spontaneous breathing).

The aerosol delivery system 10 coordinates delivery of the medicament using one or more breath sensors 34 to determine when a patient inhales and for how long. The breath sensors 34 may include a flow sensor 36 (e.g., electrical flow sensor), radar sensor 38 (e.g., UWB radar sensor for measuring chest displacement), CO2 sensor, high-speed temperature sensor 40, acoustic sensor 40, impedance plethysmography sensor 40, respiratory inductance plethysmography sensor, pressure sensor, etc. These breath sensors 34 may communicate with the controller 26 through wired connections and/or wireless connections. In some embodiments, the aerosol delivery system 10 may use a combination of breath sensors 34 (e.g., 1, 2, 3, 4, 5) to provide redundancy and/or more accurate monitoring of the patient's breathing cycle. For example, the aerosol delivery system 10 may use a flow sensor 36 in combination with a radar sensor 38 to monitor both airflow and chest movement. In another embodiment, the aerosol delivery system 10 may use a flow sensor 36, a radar sensor 38, and plethysmography sensor 40 to monitor the breathing cycle.

As illustrated, the flow sensor 36 couples to a gas delivery conduit 42 to sense changes in airflow during inhalation (e.g., mandatory, assisted, or spontaneous breathing). In some embodiments, the flow sensor 36 may also couple to a gas return conduit 44 to detect the start and end of exhalation. And in still other embodiments, the aerosol delivery system 10 may include flow sensors 36 that couple to the gas delivery conduit 42 and the gas return conduit 44. As the controller 26 receives data from the flow sensor(s) 36, the controller 26 may monitor breathing patterns to predict when the patient is going to breathe. The ability to predict when inhalation begins enables the aerosol delivery system 10 to prepare aerosolized medicament for immediate inhalation. More specifically, the aerosol delivery system 10 is able to preload fluid on a vibratable member in the aerosol generator 16 so that the fluid can be aerosolized before inhalation. Because flow detection is not a lagging indicator, the flow sensor 36 can rapidly detect unusual or spontaneous inhalation for aerosol delivery (e.g., less than 10 milliseconds from the start of inhalation).

Predicting the patient's inhalation may begin by using one or more breath and/or flow sensors 36 to tracking the patient's breathing pattern and/or a ventilation cycle (if a patient is mandatorily ventilated). The controller 26 then uses the tracked data to predict when subsequent inhalations will begin. This allows the controller 26 to direct the pump 24 to deliver fluid from the fluid source 20 to the aerosol generator 16 prior to an inhalation. The controller 26 may also signal the aerosol generator 16 to begin aerosolizing the fluid at a proper time, such as within a predetermined time period (e.g., +/−0.5 seconds) before and/or during the predicted inhalation. In this way, aerosol is ready for the patient at the start of inhalation. While the aerosol delivery system 10 is able to predict the breath cycle to produce aerosol for the patient, the aerosol delivery system 10 is also able to recognize spontaneous/irregular breathing not part of the normal pattern using the breath sensors 34. Once a spontaneous breath is recognized, the aerosol delivery system 10 may immediately pump fluid to the aerosol generator 16 for delivery to the patient.

When a patient is mandatorily ventilated (e.g., with the ventilator 14) or receives assisted ventilation, the flow sensor 36 is able to detect changes in flow as the ventilator 14 alternates between forcing air into a patient and drawing air out of the patient. The controller 26 monitors these changes in flow and then calculates when to begin aerosolizing the medicament as discussed above. In this way, the aerosol delivery system 10 can be integrated into an existing respiratory system 12 without programming or connecting the systems together. In other words, the aerosol delivery system 10 and the respiratory system 12 do not need to communicate with each other to coordinate/time aerosolization production and delivery to the patient.

It should be noted that a flow sensor 36 is more capable than a pressure sensor at detecting when a patient begins inhaling. A pressure sensor provides a lagging or delayed indicator as pressure takes time to build in an air circuit. A pressure sensor will therefore detect inhalation after the breath is over or almost over. Pressure sensors are also ineffective at determining when inhalation is complete because a pressure sensor needs a sustained inspiratory pause (i.e., plateau pressure when a patient pauses between inhaling and exhaling). Furthermore, in the event of a leak in the air circuit and/or kinks in the tubing the accuracy of pressure sensors is significantly reduced. Finally, a system that uses a pressure sensor would require a robust adaptive control algorithm to operate across mandatory, assisted, and spontaneous breathing situations because ventilator breathing creates positive pressure while spontaneous breathing creates negative pressure in the air circuit. However, in some situations a pressure sensor may be used with the aerosol delivery system 10 when the timing of aerosol production and delivery is less demanding.

Figure 2:
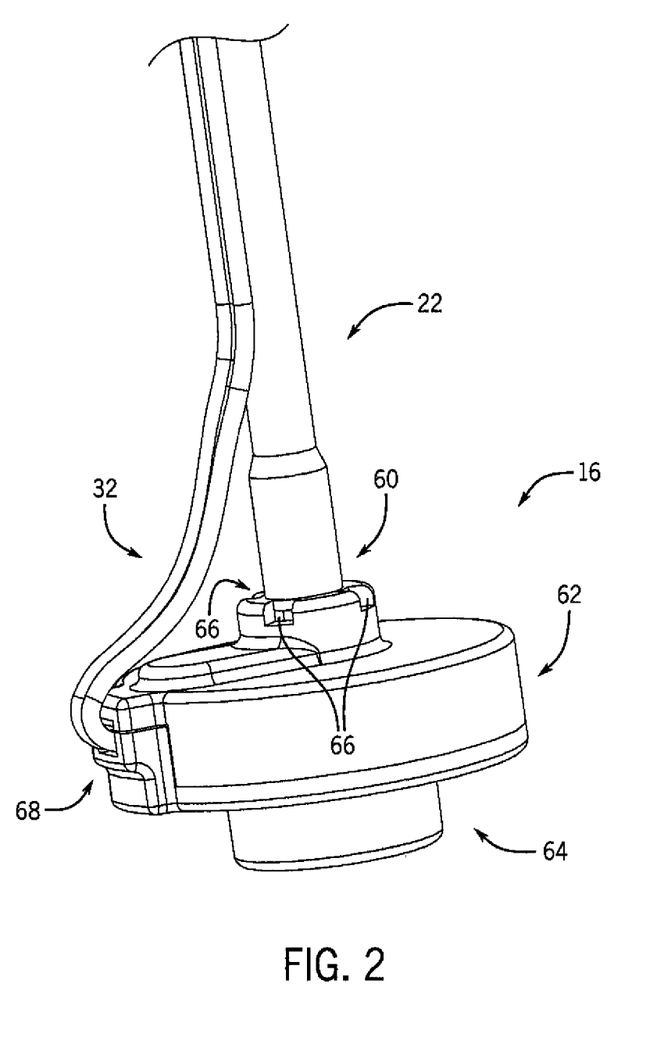
FIG. 2 is a perspective view of an embodiment of an aerosol generator.

FIG. 2 is a perspective view of an embodiment of an aerosol generator 16. As explained above, the fluid source 20 (seen in FIG. 1) fluidly couples to the aerosol generator 16 with a fluid delivery conduit 22. The fluid delivery conduit 22 couples to a fluid inlet 60 in a housing 62 of the aerosol generator 16. In operation, fluid from the fluid source 20 is pumped through the fluid inlet 60 into the aerosol generator 16 where the fluid is aerosolized. An aerosol then exits the aerosol generator 16 through a fluid outlet 64 for delivery to a patient. The outlet 64 may couple to any number of airflow devices such as endotracheal tubes, nasal cannula/masks, tracheostomy tubes, mouthpiece, etc. For example, the outlet 64 may couple to an airflow device with a snap-fit connection, press-fit connection, threaded connection, threaded fasteners, glue, weld, or a combination thereof. In some embodiments, the housing 62 may include one or more vent apertures 66 (e.g., 1, 2, 3, 4, or more). The vent apertures 66 may facilitate priming of the fluid delivery conduit 22 by enabling air to escape from the aerosol generator 16 as fluid enters the fluid delivery conduit 22. In some embodiments, the vent apertures 66 may facilitate detection of over-priming/over-pumping of fluid into the aerosol generator 16. For example, the size of the vent apertures 66 may not facilitate the rapid flow of excess fluid out of the housing 62. As pressure builds in the housing 62 from over-priming/over-pumping the controller 26 is able to detect a pressure spike. The increased pressure may be detected with a pressure sensor and/or by increased power demands by the pump 24 (seen in FIG. 1). In some embodiments, the vent apertures 66 may also facilitate aerosol production by equalizing pressure on opposing sides of the vibratable member.

In order to aerosolize the fluid, the aerosol generator electrically couples to the controller 26 (seen in FIG. 1) with a cable 32. The cable 32 couples to the aerosol generator 16 through a cable inlet 68 in the housing 62. Inside the housing 62, the cable 32 connects to a piezoelectric (or other) actuator that vibrates a vibratable member, which then aerosolizes the fluid.

Figure 3:
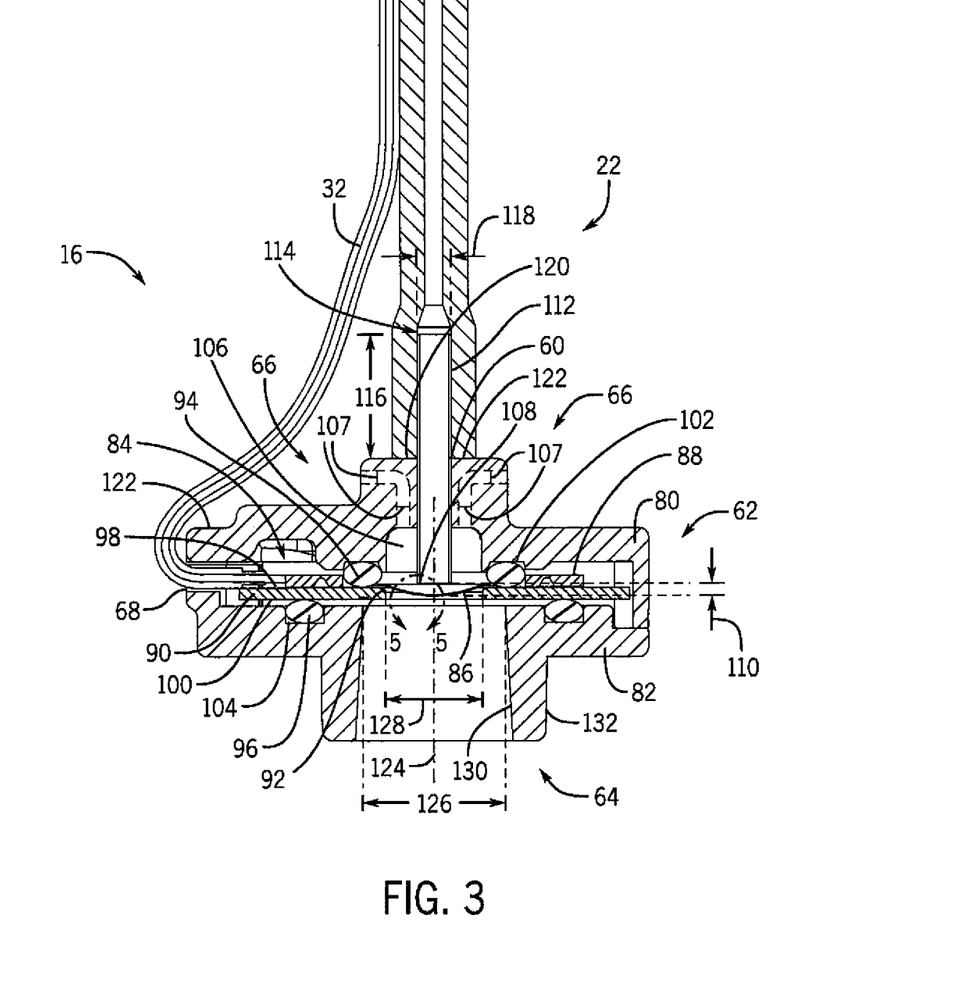
FIG. 3 is a cross-sectional view of an embodiment of an aerosol generator.

FIG. 3 is a cross-sectional view of an embodiment of an aerosol generator 16. As illustrated, the housing 62 may include a first portion 80 (e.g., first half) and a second portion 82 (e.g., second half) that couple together. The first and second portions 80, 82 may couple together with a snap-fit connection, press-fit connection, threaded connection, threaded fasteners, glue, weld, or a combination thereof. The first and second portions 80, 82 form a cavity 84 that receives the vibratable member 86 (e.g., aperture plate, mesh) and the piezoelectric actuator 88. In operation, the piezoelectric actuator 88 vibrates the vibratable member 86 by transferring energy through a support plate 90. As the vibratable member 86 vibrates it generates aerosol. In order for the aerosol to exit the aerosol generator 16, the vibratable member 86 couples to the support plate 90 around an aperture 92. The aperture 92 enables fluid communication through the housing 62 from the inlet 60 to the outlet 64 so that aerosol created by the vibratable member 86 can exit the aerosol generator 16.

The support plate 90 may be made of one or more of the following materials metal, metal alloy, polymer, etc. The vibratable member 86 may be similarly made out of a metal, a metal alloy, or a polymer. By changing the thickness of the support plate 90, the aerosol generator 16 may change the vibrational characteristics of the vibratable member 86. For example, a thicker and/or stiffer support plate 90 may resist the transfer of vibration while a thinner support plate 90 may facilitate it. In some embodiments, the support plate 90 may be a conductor (e.g., metal plate) that couples to a ground wire in the cable 32. The support plate 90 may therefore complete the circuit that powers the piezoelectric actuator 88. In some embodiments, the support plate 90 and the vibratable member 86 may be one-piece/integral instead of two separate components that couple together. In another embodiment, the vibratable member 86 may be molded over the support plate 90 (e.g., wrap around).

By indirectly coupling the piezoelectric actuator 88 to the vibratable member 86 with the support plate 90, the aerosol generator 16 is able to isolate the piezoelectric actuator 88 and cable 32 from fluid entering and exiting the housing 62. For example, the aerosol generator 16 may include a first seal 94 and a second seal 96. The first seal 94 forms a seal between a first surface 98 of the support plate 90 and the first portion 80 of the housing 62, while the second seal 96 forms a seal between a second surface 100 of the support plate 90 and a second portion 82 of the housing 62. As the support plate 90 vibrates, the seals 94, 96 are held in place within respective grooves 102, 104 (e.g., circumferential grooves) of the housing 62. In some embodiments, the seals 94, 96 may be O-ring seals made from plastic, rubber, elastomers, etc. Once assembled, the first and second housing portions 80, 82 compress the seals 94, 96 into contact with the support plate 90 forming a fluid chamber 106 as well as a fluid tight seal between the fluid chamber 106 and the piezoelectric actuator 88. These seals 94, 96 may also maintain a sterile environment by blocking contaminants from entering the fluid chamber 106 through the cable inlet 68.

As explained above, the housing 62 includes vent apertures 66. In some embodiments, the vent apertures 66 may include one or more filters 107. The filters 107 may facilitate a sterile environment by blocking contaminants from entering the fluid chamber 106. The filters 107 may also enable gas to escape from the fluid chamber 106 when priming the fluid delivery conduit 22 and block/reduce the escape of fluid from the fluid chamber 106.

The fluid chamber 106 receives fluid from the fluid delivery conduit 22 that couples to the inlet 60 of the housing 62. The fluid delivery conduit 22 extends into the fluid chamber 106 so that an outlet/end 108 of the fluid delivery conduit 22 is a distance 110 (e.g., 1 mm to 0.001 mm) from the vibratable member 86. The distance 110 ensures that the vibratable member 86 attracts fluid exiting the fluid delivery conduit 22 (e.g., through surface tension). In this way, the fluid delivery conduit 22 is able to transfer fluid to the vibratable member 86 in any orientation or substantially all orientations of the aerosol generator 16. The distance 110 may also be tuned to block or reduce the ability of the vibratable member 86 to draw/remove undispensed fluid from the fluid delivery conduit 22 (e.g., as the vibratable member 86 vibrates changing the distance 110 between the end 108 of the fluid delivery conduit 22 and the vibratable member 86). The distance 110 may also be tuned to control the spreading of fluid over the vibratable member 86. For example, the closer the fluid delivery conduit 22 is to the vibratable member 86 the greater the impact that friction between the vibratable member 86, the fluid, and the fluid delivery conduit 22 has on reducing the ability of the fluid to spread. As will be explained in additional detail below, when the fluid spreads over a greater surface area more apertures in the vibratable member 86 are exposed to fluid, which may change the characteristics of the aerosol.

The distance 110 may be controlled by how far the fluid delivery conduit 22 is inserted or able to be inserted into the housing 62. In some embodiments, the fluid delivery conduit 22 may include a connector or dispensing tip 112 (e.g., conduit, tube) that rests within the fluid delivery conduit 22 and couples to the housing 62 through the fluid inlet 60. The connector 112 may be integral with the fluid delivery conduit 22 or a separable piece. In some embodiments, the connector 112 may including a coating or treatment (e.g., wettability coating or treatment) that reduces surface energy to promote the flow of fluid through the connector to the vibratable member 86.

In embodiments with a separable connector 112, the depth 116 of the counterbore 114 as well as the overall length of the connector 112 may control the distance 110 between the connector end/outlet 108 and the vibratable member 86. In some embodiments, the fluid delivery conduit 22 may be manufactured with a plurality of connectors 112 having different lengths (e.g., a kit). These interchangeable connectors 112 enable a user to adjust the distance 110 depending on the application (e.g., type of fluid, aerosol type, different dosing rate, drug mixing, zero G use). For example, the distance 110 may increase with the viscosity of the fluid to enable the fluid to spread over the vibratable member 86 while still maintaining the attraction between the fluid and the vibratable member 86. In some embodiments, a connector 112 that reduces the distance 110 may be used to limit the spread of the fluid over the vibratable member 86, which may change the characteristics of the aerosol (e.g., smaller plume). The connectors 112 may also differ in width 118 to control the amount of fluid delivered to the aerosol generator 16 (e.g., match patient dosing). Changing the width 118 may alter dosage of the fluid by reducing or increasing the amount of fluid delivered to the aerosol generator 16 during each breath cycle. The width 118 of the connector(s) 112 may also change the characteristics of the aerosol by changing the spread of fluid over the vibratable member 86. However, minimizing the width 118 of the connector minimizes exposure of unreleased fluid to gases, contaminants, etc. Smaller widths 118 may also reduce bubble entrapment within the connector 112, which may affect dosage accuracy. Finally, minimizing the width 118 may increase the size of the fluid chamber 106.

In some embodiments, the distance 110 may be changed by inserting one or more washers (e.g., plastic, metal) between an end 120 of the fluid delivery conduit 22 and an outer surface 122 of the housing 62. In other embodiments, the system 10 may include a plurality of fluid delivery conduits 22 that have counterbores 114 at different depths 116 that enable a user to change the distance 110 with a standard sized connector 112. It should be understood that the distance changing options discussed above may be used separately or in combination with each other to change the distance 110.

As illustrated, the connector 112, inlet 60, outlet 64, and vibratable member 86 are aligned or substantially aligned with an axis 124 (e.g., center axis of the housing 62, center axis of the conduit 22, center axis of the vibratable member 86). This may facilitate the flow of fluid into the aerosol generator 16 as well as the flow of aerosol out of the aerosol generator 16. In some embodiments, the connector 112, inlet 60, outlet 64, and/or vibratable member 86 may be misaligned with respect to each other. For example, the connector 112 may be misaligned with respect to the vibratable member 86 to direct fluid over a specific area or portion of the vibratable member 86. As will be explained in detail below, the vibratable member 86 may not have uniform apertures and/or may not be uniformly vibrated. Accordingly, by directing fluid flow over a portion of the vibratable member 86 the aerosol generator 16 may change the characteristics of the aerosol. To facilitate the flow of aerosol out of the aerosol generator 16, the outlet 64 may have a width/diameter 126 that is greater than or equal to the width/diameter 128 of the aperture 92 in the support plate 90. This minimizes obstructions to the flow of aerosol out of the aerosol generator 16, which may increase the amount of aerosol delivered to the patient. In some embodiments, the outlet 64 may have a tapered interior surface 130. The tapered interior surface 130 may facilitate attachment of the aerosol generator 16 to a variety of airflow devices or sizes of a particular airflow device. In some embodiments, an exterior surface 132 of the outlet 64 may be tapered to similarly facilitate attachment of the aerosol generator 16 to different airflow devices or sizes of airflow devices.

Figure 4:
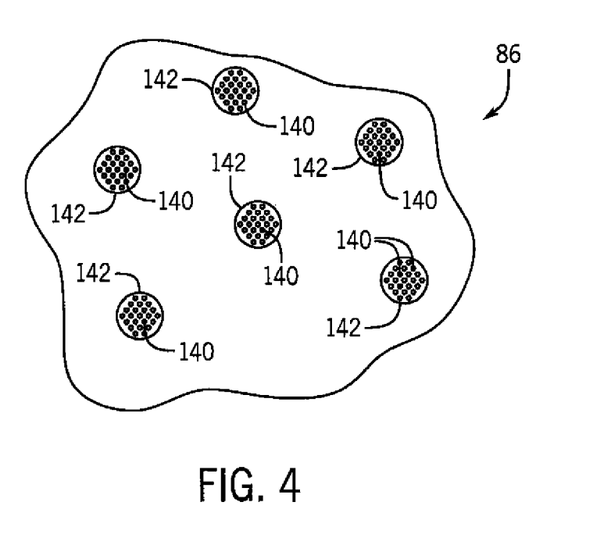
FIG. 4 is a partial top view of an embodiment of a vibratable member.

FIG. 4 is a top view of an embodiment of a vibratable member 86. As explained above the vibratable member 86 vibrates and aerosolizes the fluid in response to the piezoelectric actuator 88. The vibratable member 86 may be a photo-defined vibratable member as described in U.S. Patent Publication 2016/0130715 published on May 12, 2016 and which is hereby incorporated in its entirety for all purposes. In operation, the vibratable member 86 is capable of producing a fine particle fraction (FPF) of 99.6% or greater with droplets/particles having a volume median diameter (VMD) of 4 microns or less. In some embodiments, the aerosol generator 16 using the vibratable member 86 is capable of producing a FPF of 80% or greater with droplets having a VMD of 1 micron or less. An aerosol with these characteristics is easily suspended in and carried by a carrier fluid (e.g., air, O2, O2/air mixture, etc.) for effective delivery to a patient (e.g., deliver medicament to greater depths within the patient's lungs).

As illustrated, the vibratable member 86 includes one or more aerosolizing apertures 140 located within one or more counterbores 142. For example, each counterbore 142 may include approximately twenty apertures 140. In some embodiments, the number and/or size of the apertures 140 may differ within each counterbore 142. For example, some counterbores 142 may have five apertures 140 while others may have ten apertures 140, etc. Furthermore, the counterbores 142 may be uniformly or non-uniformly distributed over the vibratable member 86 and the apertures 140 may also be uniformly or non-uniformly distributed within the counterbore 142. The ability to vary the size, number, location, etc. of both the apertures 140 and the counterbores 142 enables adaptation to the vibrational characteristics of the support plate 90, piezoelectric actuator 88, and/or vibratable member 86. For example, the support plate 90 and/or the piezoelectric actuator 88 may vibrate portions of the vibratable member 86 more than other portions. These portions may therefore generate more aerosol than the others. Customization of the apertures 140 and counterbores 142 may therefore enable aerosol generation with different characteristics (e.g., VMD, plume velocity, plume density, average flowrate, direction, etc.). In some embodiments, customization may enable generation of different aerosols at different locations on the vibratable member 86. For example, some portions of the vibratable member 86 may generate an aerosol with a VMD of 4 microns or less while others may generate an aerosol with a VMD of 1 micron or less. The ability to customize the vibratable member 86 facilitates aerosol generation for different fluids, different treatments, different applications, etc.

Figure 5:
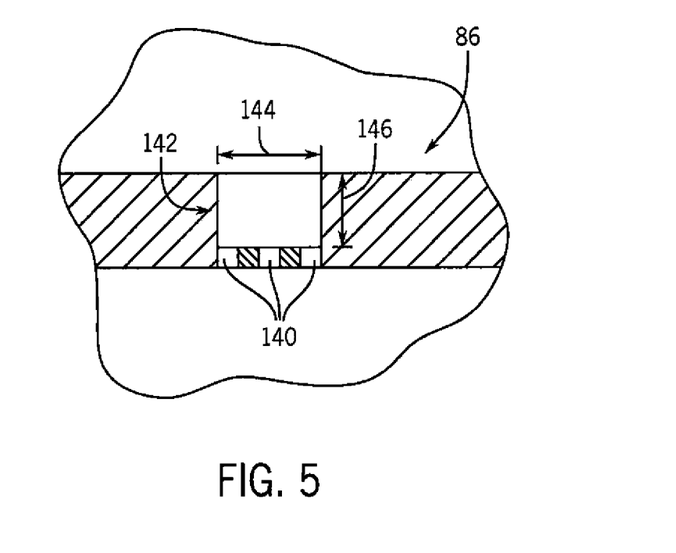
FIG. 5 is a partial cross-sectional view of an embodiment of a vibratable member within line 5-5 of FIG. 3.

FIG. 5 is a partial cross-sectional view of an embodiment of a counterbore 142 containing aerosolizing apertures 140 in a vibratable member 86 within line 5-5 of FIG. 3. As explained above, the size of the apertures 140 and counterbores 142 (including depth 146) may vary depending on the application.

Figure 6:
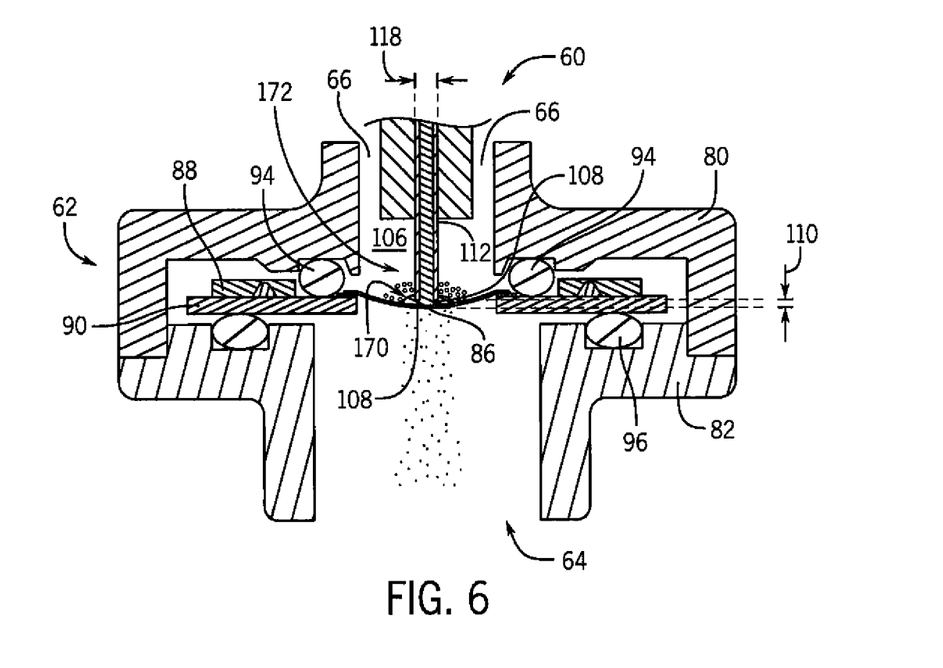
FIG. 6 is a cross-sectional view of an embodiment of an aerosol generator aerosolizing a fluid with a vibratable member.

FIG. 6 is a cross-sectional view of an embodiment of an aerosol generator 16 aerosolizing a fluid with a vibratable member 86. As explained above, the end 108 of the connector 112 may be a distance 110 away from the vibratable member 86 to ensure that the vibratable member 86 attracts the fluid exiting the fluid delivery conduit 22 (e.g., through surface tension). The distance 110 may also facilitate formation of a pool 170 that displaces obstructions so that the fluid remains in contact with the vibratable member 86 during aerosolization. For example, during aerosolization bubbles or foam 172 may form and if not displaced the foam may interfere with aerosolization of the fluid. The aerosol generator 16 therefore includes the fluid chamber 106, which provides a space for the displaced foam. The fluid chamber 106 may also reduce the creation of foam 172 while simultaneously promoting the breakdown of any foam 172 that forms.

The distance 110 may also be tuned to control the spreading of fluid over the vibratable member 86. For example, the closer the fluid delivery conduit 22 is to the vibratable member 86 the greater the impact that friction between the vibratable member 86, the fluid, and the fluid delivery conduit 22 has on reducing the ability of the fluid to spread and thus changes the properties of the aerosol (e.g., plume velocity, plume density, average flowrate, direction, etc.).

Figure 7:
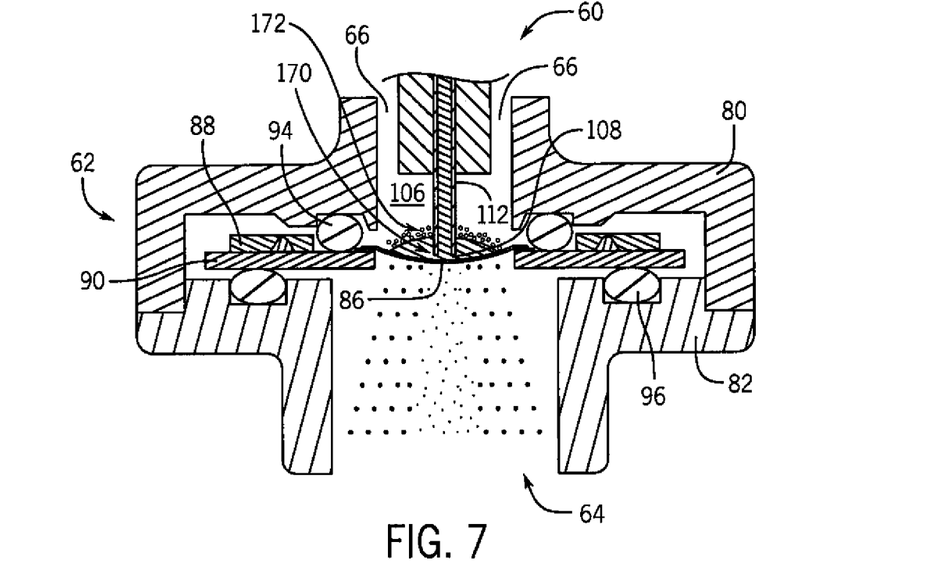
FIG. 7 is a cross-sectional view of an embodiment of an aerosol generator aerosolizing a fluid with a vibratable member.

FIG. 7 is a cross-sectional view of an embodiment of an aerosol generator 16 aerosolizing a fluid with a vibratable member 86. As explained above, the apertures 140 and counterbores 142 of the vibratable member 86 may be customized to produce aerosol with different characteristics (e.g., VMD, plume velocity, plume density, average flowrate, direction, etc.). In some embodiments, customization may enable generation of different aerosols at different locations on the vibratable member 86. As illustrated, the vibratable member 86 produced aerosol with two VMDs. For example, an outer portion of the vibratable member 86 may generate an aerosol with a VMD of 4 microns or less while an inner portion generates an aerosol with a VMD of 1 micron or less. The ability to customize the vibratable member 86 facilitates aerosol generation for different fluids, different treatments, different applications, etc.

Figure 8:
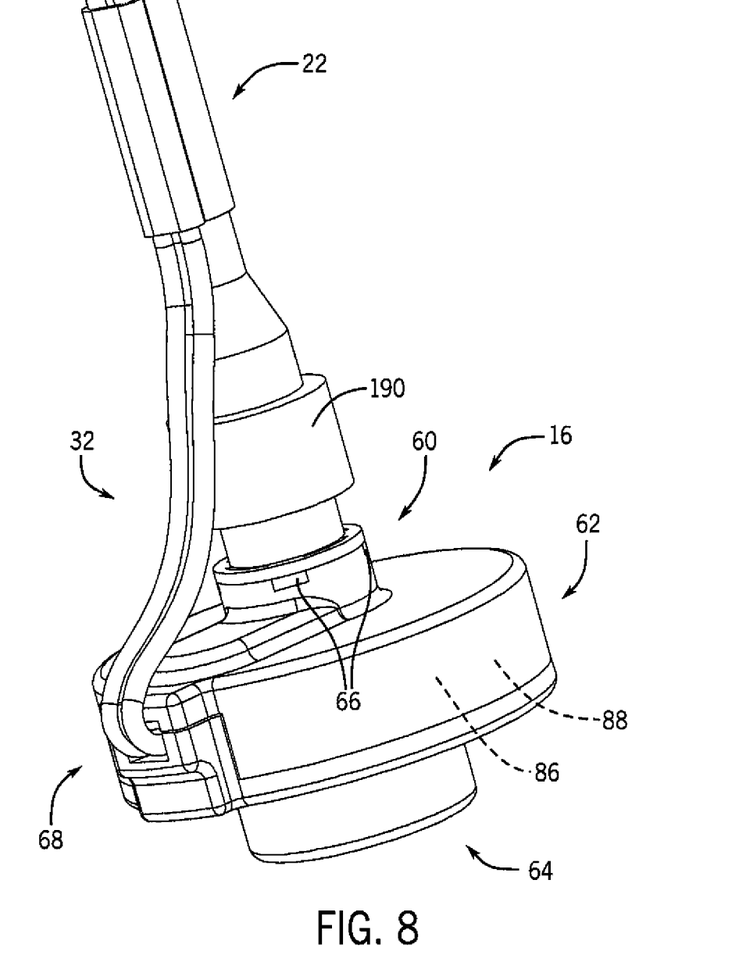
FIG. 8 is a perspective view of an embodiment of an aerosol generator.

FIG. 8 is a perspective view of an embodiment of an aerosol generator 16 with a fluid delivery conduit 22 coupled to a fluid inlet 60 in a housing 62. In operation, fluid from the fluid source 20 is pumped through the fluid inlet 60 into the aerosol generator 16 where the fluid is aerosolized and exits through a fluid outlet 64. However, instead of a single conduit delivering fluid to the vibratable member 86, the fluid delivery conduit 22 may include or couple to a manifold connector 190 containing a plurality of secondary conduits. The secondary conduits may facilitate rapid distribution of fluid over the surface of the vibratable member 86 as well as controlled distribution of liquid across the surface of the vibratable member 86 (e.g., some portions of the vibratable member 86 may receive more fluid than others).

Figure 9:
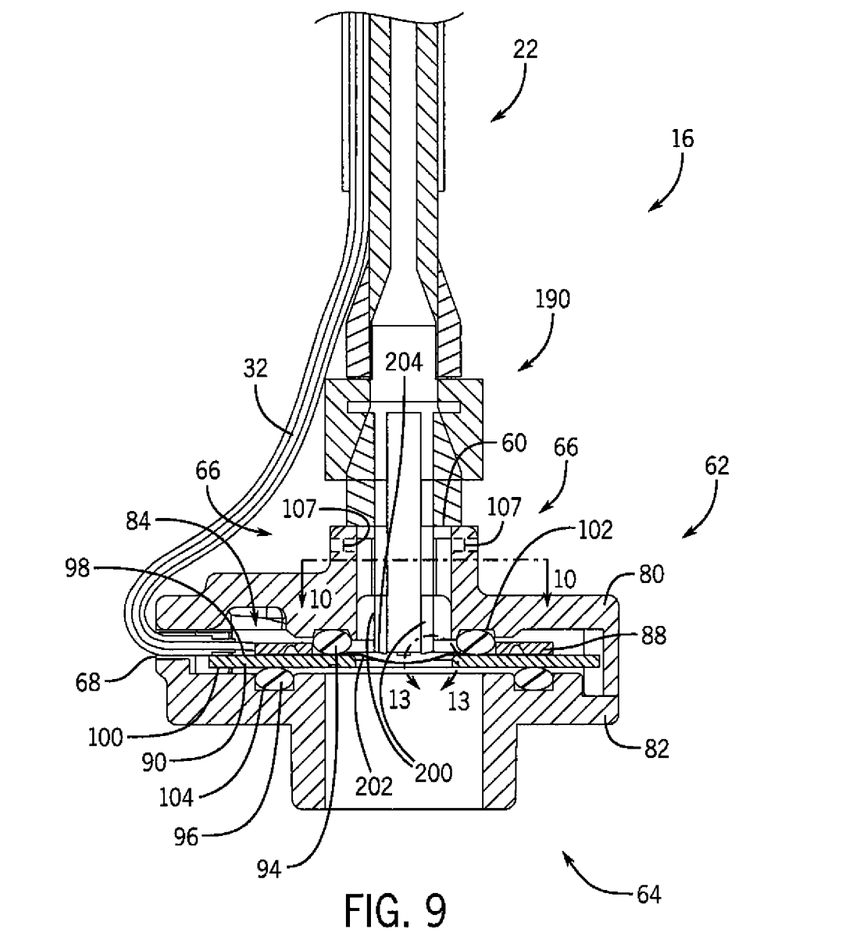
FIG. 9 is a cross-sectional view of an embodiment of an aerosol generator.

FIG. 9 is a cross-sectional view of an embodiment of an aerosol generator 16. The aerosol generator 16 may include a first portion 80 (e.g., first half) and a second portion 82 (e.g., second half) that couple together. The first and second portions 80, 82 may couple together with a snap-fit connection, press-fit connection, threaded connection, threaded fasteners, glue, weld, or a combination thereof. The first and second portions 80, 82 form a cavity 84 that receives the vibratable member 86 and piezoelectric actuator 88.

The vibratable member 86 and piezoelectric actuator 88 couple to a support plate 90 within the cavity 84. In operation, the support plate 90 enables energy transfer (e.g., vibration) from the piezoelectric actuator 88 to vibratable member 86. The support plate 90 may be made out of one or more of the following materials metal, metal alloy, polymer, etc. By changing the thickness of the support plate 90, the aerosol generator 16 may change the vibrational characteristics of the vibratable member 86. For example, a thicker and/or stiffer support plate 90 may resist the transfer of vibration while a thinner support plate 90 may facilitate it. In some embodiments, the support plate 90 may be a conductor (e.g., metal plate) that couples to a ground wire in the cable 32. The support plate 90 may therefore complete the circuit that powers the piezoelectric actuator 88.

The aerosol generator 16 may include a first seal 94 and a second seal 96 that form a seal between the first portion 80 of the housing 62 and a first surface 98 of the support plate 90 and a seal between the second portion 82 of the housing 62 and a second surface 100 of the support plate 90. As the support plate 90 vibrates, the seals 94, 96 are held in place within respective grooves 102, 104 (e.g., circumferential grooves). In some embodiments, the seals 94, 96 may be O-ring seals made from plastic, rubber, elastomers, etc. Once assembled, the first and second housing portions 80, 82 compress the seals 94, 96 into contact with the support plate 90 forming a fluid tight seal between a fluid chamber 106 and piezoelectric actuator 88. These seals 94, 96 may also maintain a sterile environment by blocking contaminants from entering the fluid chamber 106 through the cable inlet 68.

As explained above, the housing 62 includes one or more vent apertures 66. In some embodiments, the vent apertures 66 may include one or more filters 107. The filters 107 may facilitate a sterile environment by blocking contaminants from entering the fluid chamber 106. The filters 107 may also enable gas to escape from the fluid chamber 106 when priming the fluid delivery conduit 22 as well as block and/or reduce the escape of fluid from the fluid chamber 106.

The fluid delivery conduit 22 fluidly couples to the fluid chamber 106 enabling fluid to flow from the fluid source 20 to the aerosol generator 16. However, instead of a single conduit delivering fluid to the vibratable member 86, the fluid delivery conduit 22 may include or couple to a manifold connector 190 that feeds a plurality of secondary conduits 200. The secondary conduits 200 may facilitate rapid distribution of fluid over a surface 202 of the vibratable member 86 as well as controlled distribution of liquid across the surface of the vibratable member 86 (e.g., some portions of the vibratable member 86 may receive more fluid than others). The secondary conduits 200 extend into the fluid chamber 106 so that their ends/outlets 204 are a distance 110 from the vibratable member 86. The distance 110 ensures that the vibratable member 86 attracts the fluid exiting the secondary conduits 200 (e.g., through surface tension). In this way, the fluid can be transferred to the vibratable member 86 in any orientation or substantially all orientations. The distance 110 may also be tuned to block or reduce the ability of the vibratable member 86 to draw/remove undispensed fluid from the secondary conduits 200 (e.g., as the vibratable member 86 vibrates changing the distance 110 between the ends/outlets 204 of the secondary conduits 200 and the vibratable member 86). In other words, the distance 110 may facilitate accurate fluid release for aerosolization. The distance 110 may also be tuned to control the spread of fluid over the vibratable member 86. For example, the closer the secondary conduits 200 are to the vibratable member 86 the friction between the vibratable member 86, the fluid, and the secondary conduits 200 may reduce the ability of the fluid to spread. In some embodiments, one or more of the secondary conduits 200 may be placed at different distances 110 from the vibratable member 86. Accordingly, some of the secondary conduits 200 may enable more rapid spreading of fluid over portions of the vibratable member 86 while others may reduce the spread of fluid over portions of the vibratable member 86.

The manifold connector 190 may be integral with the fluid delivery conduit 22 or a separate piece. In some embodiments, the aerosol generator 16 and/or the fluid delivery conduit 22 may come with a plurality of manifold connectors 190 having secondary conduits 200 with different lengths and/or widths (e.g., a kit). These interchangeable manifold connectors 190 enable a user to change the characteristics of the aerosol produced by the vibratable member 86 including plume density, average flowrate, direction, etc.

Figure 10:
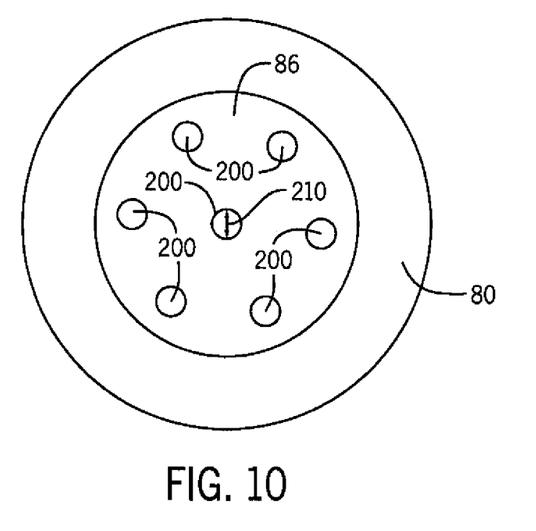
FIG. 10 is a cross-sectional view of an embodiment of an aerosol generator along line 10-10 of FIG. 9.

FIG. 10 is a cross-sectional view of an embodiment of an aerosol generator 16 along line 10-10 of FIG. 9 illustrating a plurality of secondary conduits 200 that supply fluid to the vibratable member 86. In FIG. 10, the secondary conduits 200 are equidistant apart and have equally sized aperture widths 210. While seven secondary conduits 200 are shown, it should be appreciated that some embodiments may have different numbers of secondary conduits 200 (e.g., 2, 3, 4, 5, 6, 7, 8, 9, 10, or more). In operation, the equally sized and spaced secondary conduits 200 may supply equal amounts of fluid to the entire surface 202 of the vibratable member 86. By covering a greater portion of the surface 202, the apertures 140 on the vibratable member 86 are able to aerosolize more fluid, increase the plume size, change the droplet size.

Figure 11:
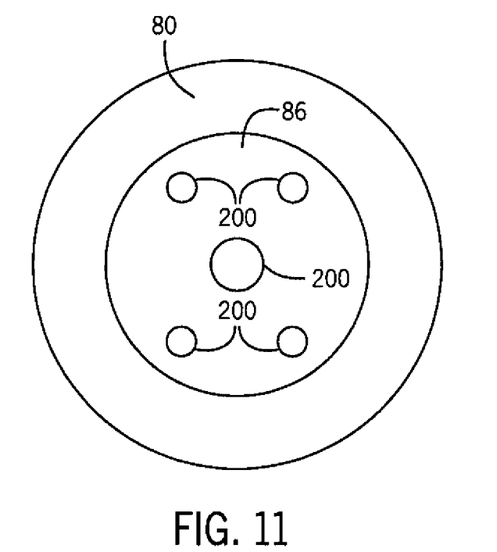
FIG. 11 is a cross-sectional view of an embodiment of an aerosol generator along line 10-10 of FIG. 9.

FIG. 11 is a cross-sectional view of an embodiment of an aerosol generator 16 along line 10-10 of FIG. 9 illustrating differently sized secondary conduits 200. For example, manifold connector 190 may include a secondary conduit 200 centered on the vibratable member 86 with smaller secondary conduits 200 surrounding the centrally located secondary conduit 200. However, in other embodiments the size and location of the secondary conduits 200 may differ (e.g., smaller secondary conduits 200 concentrated near the center of the vibratable member 86 and larger secondary conduits 200 positioned around the perimeter). By including differently sized secondary conduits 200, the manifold connector 190 is able to increase fluid flow to portions of the vibratable member 86. As explained above, the vibratable member 86 may not vibrate equally over the entire surface 202 and/or the concentration of apertures 140 may not be equally dispersed. Accordingly, positioning differently sized secondary conduits 200 over the vibratable member 86 may enable production of an aerosol with the desired characteristics (e.g., droplet size, output rate, appropriate velocity of exiting droplets).

Figure 12:
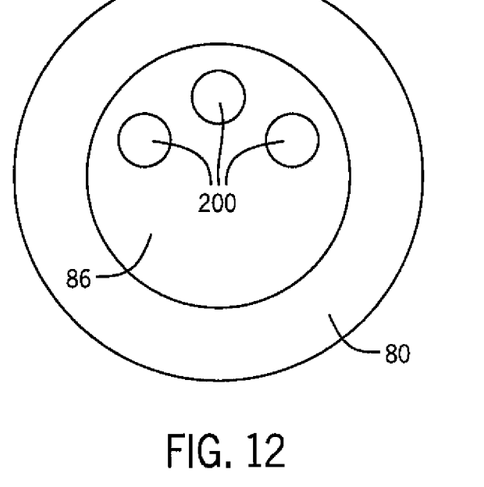
FIG. 12 is a cross-sectional view of an embodiment of an aerosol generator along line 10-10 of FIG. 9.

FIG. 12 is a cross-sectional view of an embodiment of an aerosol generator 16 along line 10-10 of FIG. 9. Because the vibratable member 86 may not vibrate equally over the entire surface 202 and/or the concentration of apertures 140 may not be equally dispersed the secondary conduits 200 may be concentrated in particular locations. In FIG. 12, the aerosol generator 16 includes secondary conduits 200 that are concentrated over a portion of the vibratable member 86. While three secondary conduits 200 are illustrated, other embodiments may have a different number of secondary conduits 200 (e.g., 2, 3, 4, 5, 6, 7, 8, 9, 10 or more). The secondary conduits 200 may also have different sizes with respect to each other.

Figure 13:
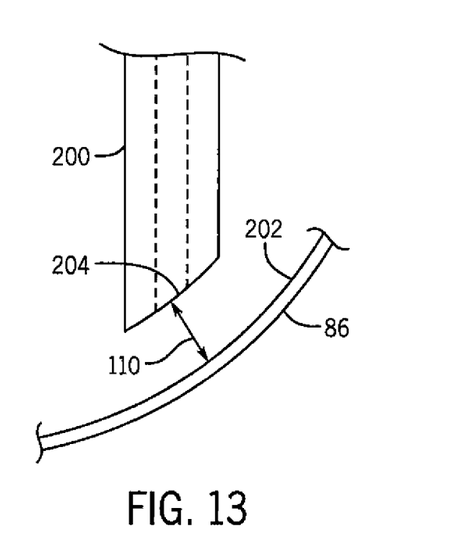
FIG. 13 is a sectional view of an embodiment of a secondary conduit within line 13-13 of FIG. 9.

FIG. 13 is a sectional view of an embodiment of a secondary conduit 200 within line 13-13 of FIG. 9. As explained above, the distance 110 between the outlet 204 and the surface 202 of the vibratable member 86 facilitates attachment of the fluid to the vibratable member 86 as well as control the spread of fluid. In some embodiments, the vibratable member 86 may be concave. In order to maintain the distance 110 between secondary conduits 200 positioned away from a center of the vibratable member 86, the secondary conduits 200 may have angled or tapered ends/outlets 204 that maintain an appropriate distance 110 between the secondary conduit 200 and the vibratable member 86. Angles of the tapered ends/outlets 204 may be straight and/or curved. For example, one or more of the tapered ends/outlets 204 may have a contour that mimics a contour of the surface 202 of the vibratable member at a position below the particular tapered end/outlet 204.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An aerosol delivery system, comprising:
an aerosol generator, comprising:
a housing having a housing inlet and a housing outlet, wherein the housing defines a chamber fluidly coupled to the housing inlet and the housing outlet, wherein the housing defines a vent aperture that extends through a thickness of the housing and is fluidly coupled to the chamber, and wherein the vent aperture is configured to vent at least one of gas, liquid, and foam from the housing;
a support plate operably coupled to the housing, wherein the support plate defines an aperture;
a vibratable member operably coupled to the support plate so as to be positioned across the aperture;
a piezoelectric actuator coupled to the support plate, wherein the piezoelectric actuator expands and contracts to vibrate the vibratable member which aerosolizes a fluid;
a first seal that is disposed between the chamber and an inner surface of the piezoelectric actuator;
a second seal that is disposed on an opposite side of the support plate as the first seal, the second seal being disposed between the chamber and a power connection of the aerosol generator; and
a fluid conduit having a distal end spaced apart from the vibratable member so as to be configured to deliver the fluid to the vibratable member, wherein the distal end of the fluid conduit is positioned about 1.0 mm to about 0.001 mm from the vibratable member to facilitate adhesion of substantially all of the delivered fluid to the vibratable member using surface tension forces regardless of an orientation of the housing until the fluid is aerosolized by vibration of the vibratable member.

2. The system of claim 1, wherein the fluid conduit comprises a connector conduit, wherein the fluid conduit couples to a fluid source.

3. The system of claim 2, wherein the connector conduit passes through the housing inlet and rests within the chamber.

4. The system of claim 1, wherein the fluid conduit comprises one of a plurality of fluid conduits within the housing that are usable to supply fluid to the vibratable member.

5. The system of claim 1, comprising a first seal that seals between the housing and the support plate.

6. The system of claim 5, comprising a second seal that seals between the housing and the support plate, wherein the first and second seals seal against opposing sides of the support plate.

7. The system of claim 1, wherein the housing comprises a first portion and a second portion that couple together, and wherein the first portion defines the housing inlet and the second portion defines the housing outlet.

8. The system of claim 1, wherein the vibratable member and the support plate are integral.

9. The system of claim 1, comprising a controller configured to control delivery of the fluid to the vibratable member through the fluid conduit.

10. An aerosol delivery system, comprising:
an aerosol generator, comprising:
  a housing defining a fluid chamber that fluidly communicates with a housing inlet and a housing outlet;
  a support plate coupled to the housing, wherein the support plate defines an aperture in fluid communication with the housing outlet;
  a vibratable member coupled to the support plate around the aperture;
  a piezoelectric actuator coupled to the support plate, wherein the piezoelectric actuator expands and contracts to vibrate the vibratable member which aerosolizes a fluid; and
  a plurality of conduits that deliver the fluid to the vibratable member, wherein:
    each of the plurality of conduits comprises sidewalls that define a lumen that comprises an open inlet end and an open outlet end;
    the sidewalls close the lumen along a length to define a closed fluid path that extends along the length from the open inlet end to the open outlet end; and
    the open outlet end of each lumen is spaced apart from the vibratable member.

11. The system of claim 10, wherein the plurality of conduits are included within a manifold.

12. The system of claim 10, wherein at least one of the conduits of the plurality of conduits differs in size from the remaining conduits.

13. The system of claim 10, wherein at least one of the plurality of conduits comprises an angled outlet.

14. The system of claim 13, wherein the angled outlet is shaped to match a shape of a portion of a surface of the vibratable member that faces and is aligned with the angled outlet.

15. The system of claim 10, wherein a distal tip of each of the plurality of conduits is spaced apart from a surface of the vibratable member by between about 0.001 mm and 1 mm such that the fluid adheres to the surface by surface tension forces.

* * * * *